United States Patent [19]
Thoma

[11] Patent Number: 5,177,662
[45] Date of Patent: Jan. 5, 1993

[54] CAPACITANCE HUMIDITY SENSOR

[75] Inventor: Paul E. Thoma, Cedarburg, Wis.

[73] Assignee: Johnson Service Company, Milwaukee, Wis.

[21] Appl. No.: 831,553

[22] Filed: Feb. 5, 1992

[51] Int. Cl.$^5$ .......................... H01G 5/20; H01G 7/00; G01W 1/00
[52] U.S. Cl. .................................. 361/286; 29/25.42; 73/335.6
[58] Field of Search ............... 361/286, 323; 73/336.5, 73/335; 29/25.42

[56] References Cited

U.S. PATENT DOCUMENTS

| | | | |
|---|---|---|---|
| 3,458,845 | 7/1969 | Thoma | 338/35 |
| 3,582,728 | 6/1971 | Thoma | 73/336.5 |
| 3,697,450 | 10/1972 | Takenaka | 252/511 |
| 3,802,268 | 4/1974 | Thoma | 73/336.5 |
| 4,564,882 | 1/1986 | Baxter et al. | 361/286 |
| 4,965,698 | 10/1990 | Thoma et al. | 361/286 |
| 5,050,434 | 9/1991 | Demisch | 73/336.5 |
| 5,069,069 | 12/1991 | Miyagishi et al. | 73/335 |

OTHER PUBLICATIONS

IEEE Transactions on Components, Hybrids, and Manufacturing Technology, vol. CHMT-2, No. 2, Sep. 1979, pp. 321-323

Primary Examiner—Donald A. Griffin
Attorney, Agent, or Firm—Foley & Lardner

[57] ABSTRACT

A capacitance humidity sensor according to the invention has a film core which is in contact with a pair of polymeric conductive layers bonded to opposite faces of the core. The core is made of a polymeric material having a dielectric constant which varies substantially linearly with humidity, such as a polyimide or polyparabanic acid. The conductive layers are made of a polymeric material, at least a portion of which includes sulfur atoms in the backbone chain and having conductive particles, such as carbon particles, dispersed therein. Such conductive layers provide superior performance and corrosion resistance in comparison to the metal films employed in the prior art and in comparison to cellulosic polymers containing conductive particles.

20 Claims, 5 Drawing Sheets

CAPACITANCE HUMIDITY SENSOR

BACKGROUND OF THE INVENTION

1. Field of the Invention

The invention relates generally to capacitance humidity sensors, particularly to humidity sensors having a moisture sensitive dielectric layer interposed between a pair of conductors, and still more particularly to the use of polymers having sulfur atoms in their backbone chains as the resin matrix for the conductor layers.

2. Description of the Prior Art

In commonly-owned U.S. Pat. No. 4,965,698 issued Oct. 23, 1990 to Thoma, et al. for "Capacitance Humidity Sensor", hereafter the '698 patent, a device of the general type with which the present invention is concerned is described in considerable detail. The device of the '698 patent includes a core made of a material whose dielectric constant varies substantially linearly with humidity, such as a polyimide or polyparabanic acid material. The core is sandwiched between layers of polymeric material having conductive particles, such as conductive carbon particles, dispersed therein. In the '698 patent, the resin matrix for the conductive layers is described as containing certain crosslinked polymers formed by the reaction of a compound containing glucoside chains and a monomer or partial polymer capable of reacting with the hydroxyl groups of the glucosides. Specific examples of the disclosed materials included cellulose nitrate, cellulose triacetate, cellulose butyrate and, most preferably, cellulose acetate butyrate (CAB) crosslinked with urea formaldehyde or melamine formaldehyde.

Reference was also made in the background section of the '698 patent to other types of known humidity sensors which included a dielectric layer and thin metal electrode conducting layers. Reference should be made to the patents cited in column 1 of the '698 patent for examples of such systems. The prior systems discussed in the earlier patent were deemed to have poor corrosion resistance, since thin metal electrodes could rapidly be destroyed by sulfur-based pollutants or chlorine.

Polyimides have been recognized as a particularly useful dielectric for such sensors because the dielectric constant is linearly proportional to the moisture content. However, bonding between the polyimide and prior art metal foil electrode layers was difficult without the use of adhesives because of the dissimilarity between the metal and plastic.

The '698 patent also discusses the use of mixtures of conductive particles, such as particles of silver or carbon black, dispersed in resins such as polyimides as shown, for example, in the Takenaka, U.S. Pat. No. 3,697,450 issued Oct. 10, 1972. It was also pointed out that other humidity sensors have employed various layers of crosslinked resins such as CAB crosslinked with urea formaldehyde. In one sensor, a crosslinked cellulose acetate butyrate core, containing conductive particles such as carbon, is sandwiched between a pair of outer resin layers free of carbon particles. See Thoma, U.S. Pat. No. 3,458,845 issued Jul. 29, 1969. In other humidity sensors, the outer resin layers contain the conductive particles and the inner resin layer does not; see Thoma, U.S. Pat. Nos. 3,582,728 issued Jun. 1 1971; 3,802,268 issued Apr. 9, 1974; and *IEEE Transactions On Components. Hybrids and Manufacturing Technology*, Vol. CHM2-2, No. 3, 1979, pgs. 321-323. Baxter, et al. U.S. Pat. No. 4,564,882 issued Jan. 14, 1986 describes a humidity sensing element wherein the dielectric layer can be made from either CAB or polyimide. Reference should also be made to the prior Thoma, et al. patent for discussions on the background use of polyparabanic acid polymers and on screen printing technologies.

The present invention addresses certain remaining drawbacks with capacitance humidity sensors, such as the ones disclosed in the '698 patent. Specifically, it is desirable to improve the bonding between the conductive layers and the dielectric to prevent delamination which can occur during use as a result of changing temperatures and humidities.

SUMMARY OF THE INVENTION

A capacitance humidity sensor according to the present invention has a dielectric core in contact with a pair of conductors. In its preferred aspect, the core is made of a material having a dielectric constant which varies substantially linearly with humidity and the conductive layers are made from a resin material having conductive particles dispersed therein. The preferred resin material is one which includes sulfur atoms in its backbone chain, such as polysulfones and polyethersulfones. These polymers have similar thermal and hygroscopic expansion coefficients, when compared to the heterocyclic polymers used in the preferred dielectric layers, and thus resist delamination during use. In the preferred embodiment, the conductive layers are applied to the dielectric film by screen printing directly on both sides of the film.

DETAILED DESCRIPTION OF THE PREFERRED EMBODIMENT

Figure 1:
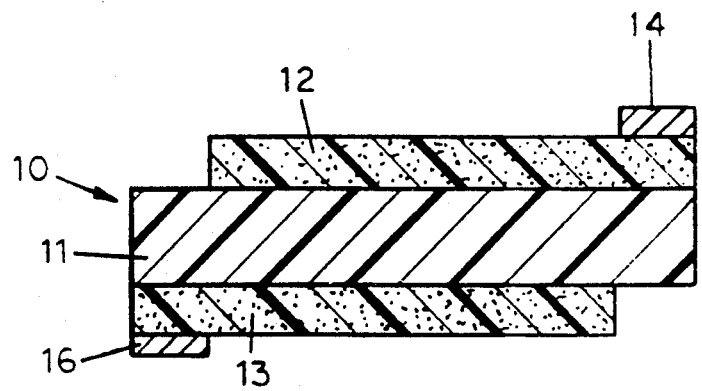
FIG. 1 is a cross-sectional view of a humidity sensing element according to the present invention.

The present invention provides a capacitance humidity sensor element in the form of a thin, flexible film. Referring to FIG. 1, humidity sensor 10 according to the invention includes a dielectric film core 11 having a pair of electrically conductive layers 12, 13 on opposite sides thereof. Silver contacts 14, 16 on layers 12, 13 connect the sensor element to a source of electrical current. According to one aspect of the invention, the specific plastics used for the construction of film 11 and layers 12, 13 are made to give the sensor element 10 advantageous properties in a manner not achieved previously.

Dielectric film 11 is a water absorbing material having a dielectric constant which changes predictably (preferably, essentially linearly) as a function of relative humidity. A specific class of polymers is especially useful as the dielectric layer of the humidity sensor of the invention. Each of the members of the class have backbone chains containing heterocyclic units in which one or more atoms in the heterocyclic unit is nitrogen, one or more carbon atoms in the heterocyclic unit has an oxygen atom double bonded to it (i.e., the unit contains one or more keto groups), and the heterocyclic unit is bonded into the polymer backbone through one or more nitrogen atoms of the heterocyclic ring. Suitable materials for use as film 11 are described in detail in the aforementioned '698 patent, including structural formulations. They include the general class of polyimides and polyparabanic acids which have been found to be particularly useful because the hysteresis curves for such resins are substantially linear under a broad range of conditions, as illustrated in the graphs provided therein. The resulting change in capacitance for a given change in humidity is remarkably constant over a temperature range of about 15° C. to 50° C., allowing the humidity sensor to be employed in harsh conditions.

The dielectric film may be made as thin as possible for the desired capacitance and film strength, and, unlike many known sensors, can be thinner by half or more than the conductive layers. Film 11 can, for example, have a thickness of 0.005 inch or less, especially 0.0005 inch or less.

The resulting element 10 is extremely light and thin, and represents a departure from many prior sensors which employ a rigid base. According to the method of the invention described in the '698 patent, a film comprising the dielectric layer is made prior to the formation of the outer, integrally bonded conducting layers. Since the dielectric core is prepared as a separate film, its thickness, electrical properties and composition can be closely controlled.

Figure 2:
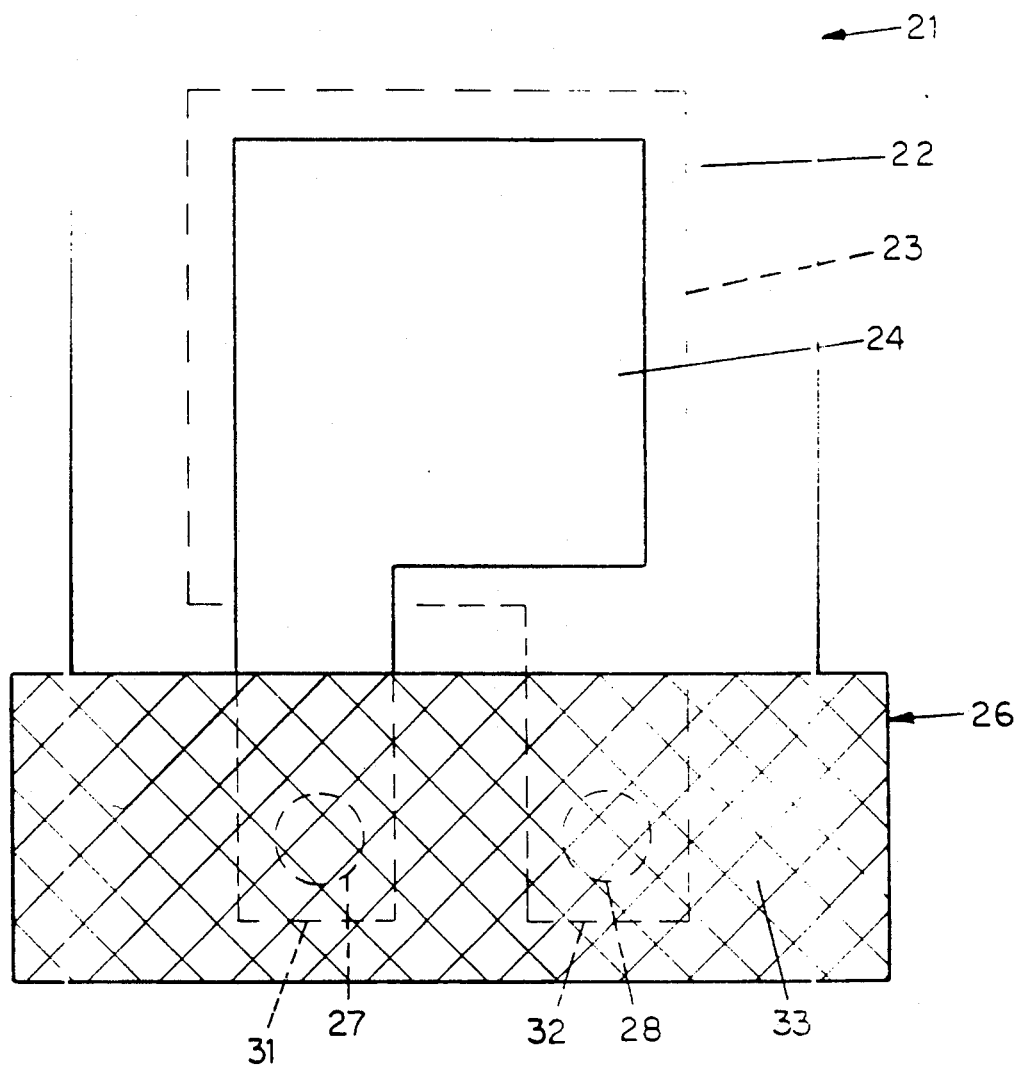
FIG. 2 is a top view of a humidity sensor according to the invention.

FIG. 2 illustrates a humidity sensor 21 according to the invention. Sensor 21 includes a dielectric film 22 made of the polymeric film described above, a pair of conductive layers 23, 24 formed on opposite sides of film 22, and a holder 26. Outer conductive layers 23, 24 form the plates of the capacitor. Layers 23, 24 cover selected areas on opposite sides of dielectric film 22. The overlapping areas of the conductive layers 23, 24 comprise the active portion of the capacitance humidity sensor. Spots 27, 28 of conductive material, such as silver paint, are applied over conducting layers 23, 24 in areas where the layers 23, 24 do not overlap, for example in elongated tab portions 31, 32, which extend into holder 26. Electrical contact is made to spots 27, 28 by means of one or more conductive metal plates 33 forming part of holder 26 used to mount the humidity sensor.

Humidity sensing element 21 may be used in combination with a variety of conventional circuitry to provide a humidity sensor, such as the ones described in Thoma, U.S. Pat. Nos. 3,582,728 and 3,802,268, as well as Carusillo, U.S. Pat. Nos. 4,558,274 and 4,661,768, the entire contents of which are hereby incorporated by reference. Such systems generally include the sensing element 21, a humidity indicator, such as a meter, a power source, and circuitry for interconnecting the above. The indicator provides a visual indication of changes in relative humidity as related to dielectric constant changes in the dielectric film.

The techniques for forming the humidity sensor are also described in the aforementioned '698 Thoma, et al. patent, including the steps of forming the dielectric layer and the application of the conductive layers thereto. Generally, conductive layers 12, 13 and 23, 24 will be identical to one another, although for some applications, the thickness or electrical conductivity thereof may be varied. Screen printing is a particularly useful method for applying the compositions to the film, which can be held in place by suction applied through a fine screen holder positioned beneath the film. A stencil is placed over the film and the film is screen printed using conventional equipment, following which solvent is removed, thus resulting in a fusion of the conductive layers to the dielectric.

Dealing now with the conductive layers of the present invention, conductive particles are typically used in conductive layers 12, 13 and 23, 24, which should each have a resistivity of about 50,000 $\Omega/\square$ or less, preferably 15,000 $\Omega/\square$ or less, as compared to dielectric film 11, which generally has a resistivity of at least about $10^{13}$ ohm-cm, preferably at least about $10^{15}$ ohm-cm at 25° C. and 50% relative humidity. The preferred conductive particles for the present invention are those set forth in the aforementioned '698 patent, including carbon particles, particularly those which have long chains of particles to form agglomerates having an average agglomerate size of 10 microns, and preferably 0.25 micron or less. The conductive particles are generally used in an amount in the range of about 10-80 wt./%, the balance being the polymeric matrix to be described shortly. The conductivity of the particles can be enhanced by heating in vacuum, although heating in vacuum is not essential. Carbon particles, such as Vulcan ® XC-72 made by the Cabot Corporation, is one particularly preferred conductive material.

The thickness of layers 12, 13 also influences the response time of the sensor, as does the molecular structure of the conductive layers, which is designed to have a high level of water transmission. The layers ideally should have a thickness of 0.01 inch or less, particularly 0.001 inch or less, to allow sufficiently rapid response time, e.g. 15 minutes or less.

The matrix for the conductive particles used in the preparation of conductive layers 12, 13 and 23, 24 are preferably selected from resins which include sulfur atoms in their backbone chains. These polymers are moisture pervious, i.e., they transmit water molecules to the dielectric layer and they bond securely to the dielectric film.

To achieve such integral bonding between the conductive layers and the dielectric core, physical and/or chemical bonds must exist between the layers. Sulfur containing polymers, such as polysulfone and polyethersulfones, are highly effective as the polymeric matrix for the conductive layer. These polymers have been found to have similar thermal and hygroscopic expansion coefficients as the heterocyclic polymers used in the dielectric layer and thus resist delamination during use due to changing temperature and relative humidities. Other sulfur containing polymers for the polymer matrix of the conductive layers within the scope of this invention include polyarylsulfones and polyphenylsulfones.

Sulfur containing polymers, such as polysulfone, can be bonded to a polyimide dielectric core by applying the polysulfone to the core layer as a solvent solution, and then heating the solution to a temperature at or above the glass transition temperature, Tg, of the polysulfone. A temperature of 190° C. to 325° C. for 30 minutes fuses polysulfone to the dielectric core to form a strong, adhesive bond between the conductive layer and the dielectric core.

EXAMPLE 1

The following procedure was used to fabricate a film-type capacitance humidity sensor. The dielectric polymer in this example was Kapton®HN PMDA-ODA polyimide (pyromellitic dianhydride-p,p'-oxydianiline polyimide), and the electrically conductive humidity transmitting layers were composed of polysulfone and deoxidized carbon.

The liquid formulation for the conductive layers included the following chemical composition, by weight:

61.5 wt./% (100.0 g) bromochloromethane
27.7 wt./% (45.0 g) butyrophenone
2.5 wt./% (4.0 g) deoxidized Vulcan XC-72 carbon
8.3 wt./% (13.5 g) polysulfone The above composition was mixed on a ball mill for 7 days. This process breaks up the carbon pellets and disperses the carbon particle aggregates in the liquid to create a liquid-solid suspension. The mixture was then vacuum evaporated to a viscosity of 450,000 to 500,000 cps on a Brookfield Digital Viscometer. The conductive composition was then ready for application to the dielectric film.

EXAMPLE 2

Another composition was prepared, similar to that of Example 1, except that a single solvent was used and the polysulfone was added in a two-step process. The first step in making the formulation consists of mixing together the following:

91.7 wt./% (100.0 mls = 102.1 g) butyrophenone
6.5 wt./% (7.2 g) deoxidized Vulcan XC-72 carbon
1.8 wt./% (2.0 g) polysulfone These were mixed together on a ball mill for 7 days at 150-170 rpm to disperse the carbon in the solution. 18.5 grams (16.6 wt./% of the initially prepared solution) of polysulfone was then added to the solution and the components were mixed on the ball mill at very slow speed for an additional 16 hours or until the additional polysulfone was dissolved. The resulting medium viscosity formulation (21,000 cps) was used to make the conductive layers of a humidity sensor element having Upilex®R BPDA-ODA polyimide (sym-biphenyl tetracarboxylic acid dianhydride-p,p'-oxydianiline polyimide) film as the dielectric core in the same manner as described in Example 1.

The conductive solutions prepared in Examples 1 and 2 would be used in the formulation of a humidity sensor in the fashion described in the aforementioned '698 patent, which formulation procedure is again incorporated specifically by reference herein and will not be repeated.

Figure 3:
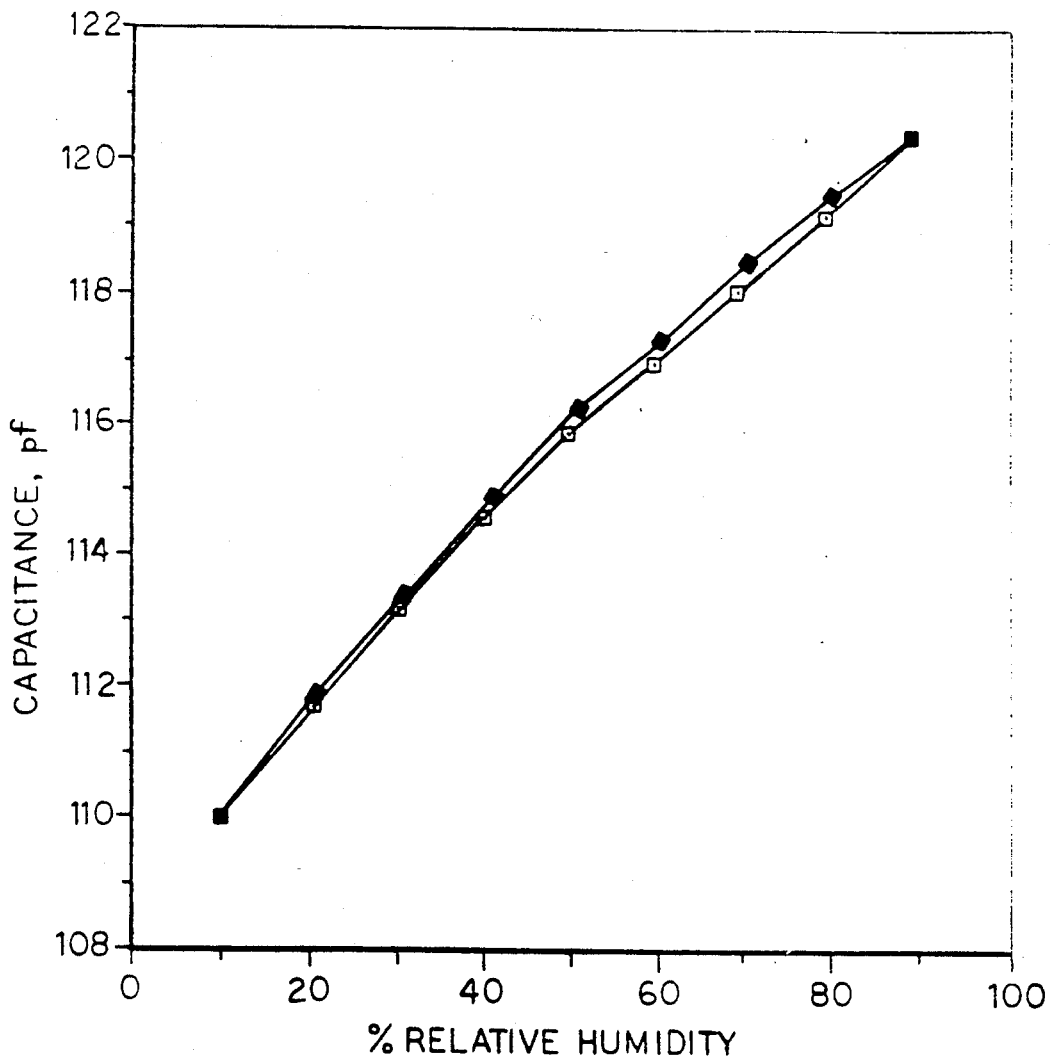
FIG. 3 is a graph plotting relative humidity vs. capacitance in picofarads for a humidity sensor according to the invention.
Figure 4:
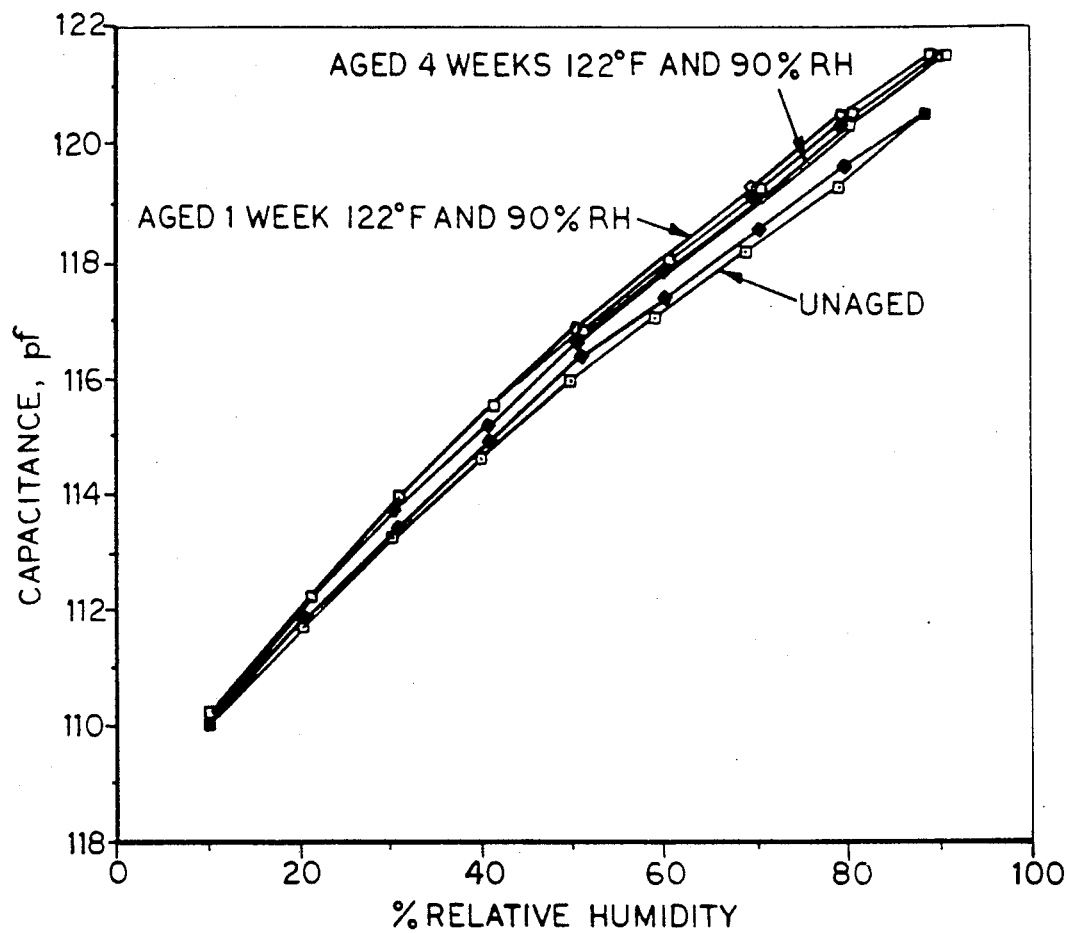
FIG. 4 is a graph plotting relative humidity vs. capacitance in picofarads for a humidity sensor according to the invention at three different aging time periods at 122° F. and 90% relative humidity following manufacture.

Referring now to FIGS. 3 and 4, the advantages of the present invention can be readily appreciated. FIG. 3 is a graph comparing relative humidity and capacitance in picofarads of a capacitor having a Upilex®R dielectric core with polysulfone matrix conductive plates, prepared in accordance with Example 2. As can be noted in this graph, the capacitance is substantially linear throughout the disclosed relative humidity range.

FIG. 4 is a graph of the same material, in an unaged condition and aged for one week and four weeks at 90% relative humidity and 122° F. Capacitance remains substantially linear with relative humidity over the time periods measured.

Figure 5:
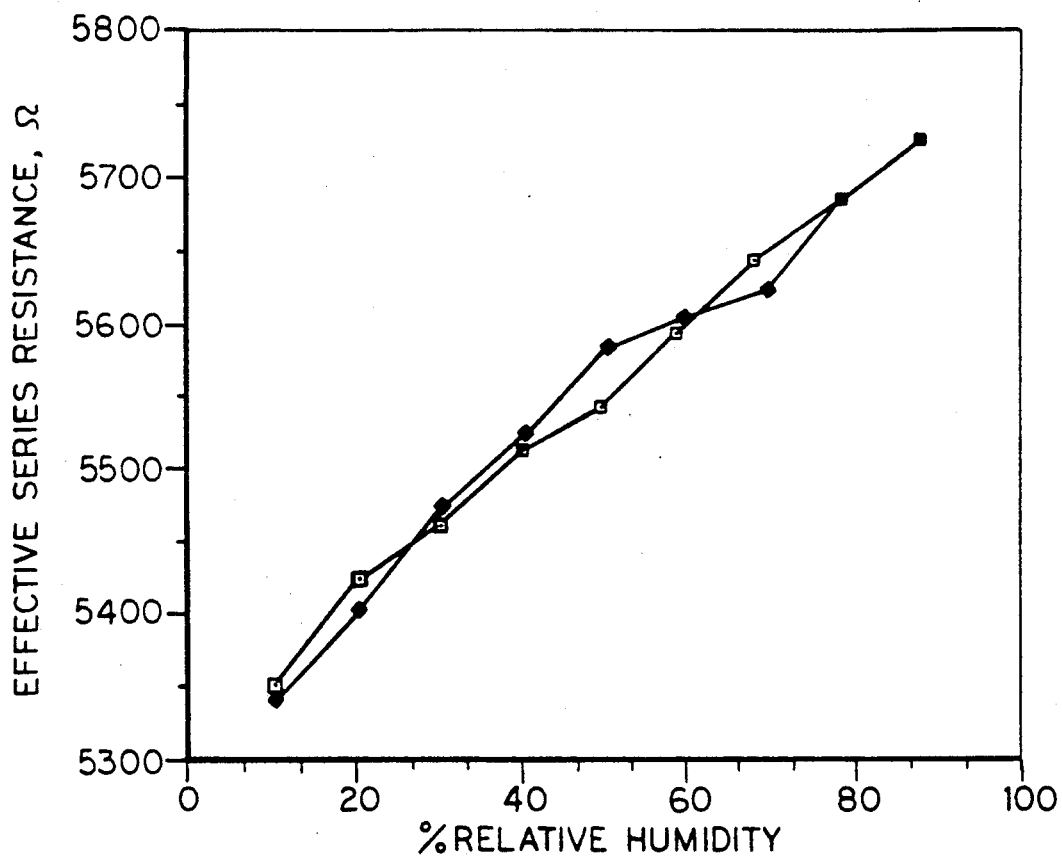
FIG. 5 is a graph plotting relative humidity vs. effective series resistance in ohms for humidity sensors according to the present invention.

FIG. 5 is another comparison of the materials shown in FIGS. 3 and 4, this time using effective series resistance in ohms. The results are also deemed to be highly desirable.

Figure 6:
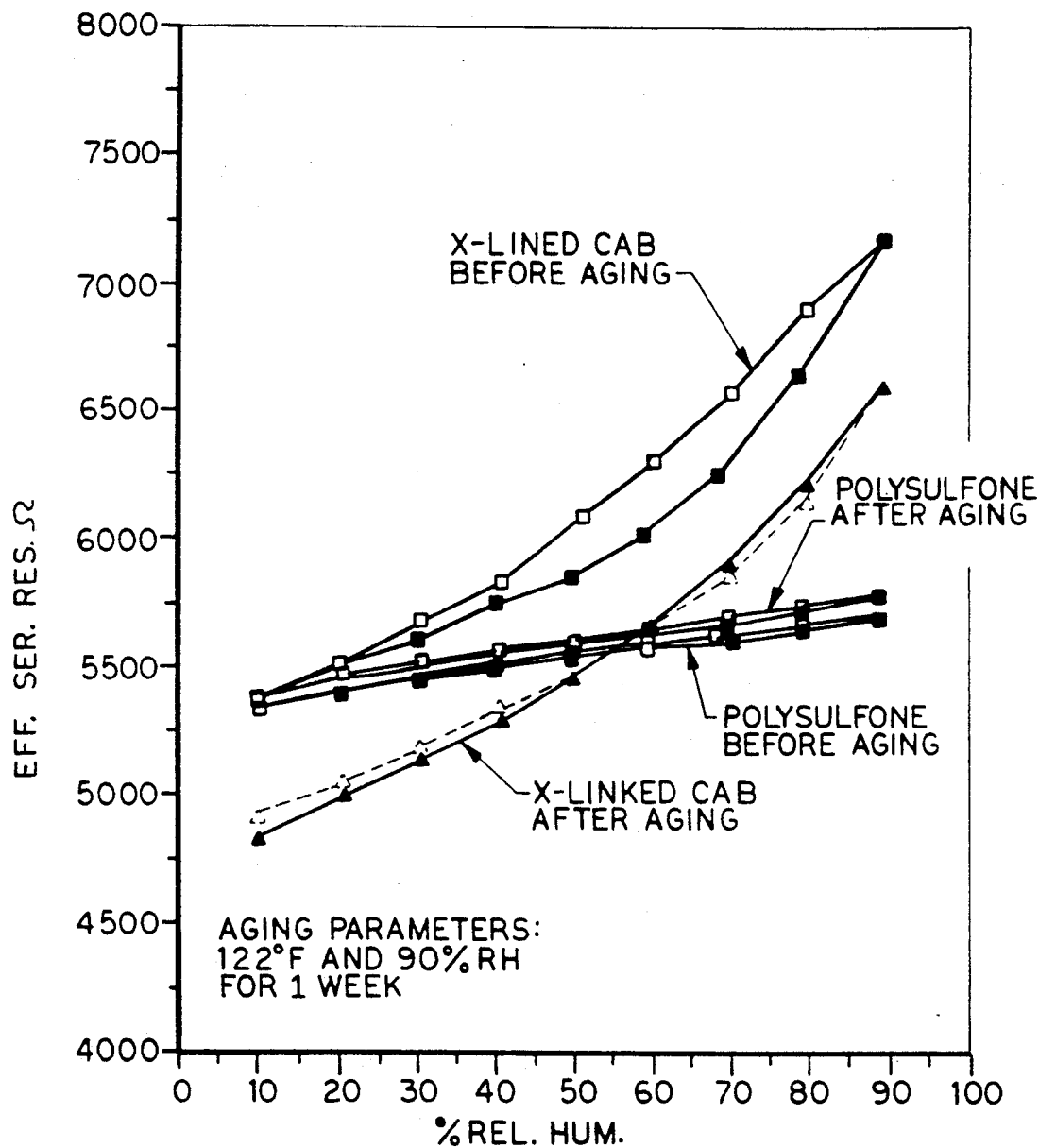
FIG. 6 is a graph comparing percent relative humidity vs. effective series resistance in ohms for CAB type humidity sensors and polysulfone humidity sensors unaged and after aging for one week at 122° F. and 90% relative humidity.

The final graph, FIG. 6, is a comparison of the effective series resistance in ohms of a capacitor with Upilex®R as the dielectric layer and polysulfone as the polymer matrix of the conductive layers, compared to a Kapton® HN as the dielectric layer and crosslinked CAB as the polymer matrix of the conductive layers as disclosed in Example 1 of the '698 patent. It can be noted that the effective series resistance of the capacitor made with polysulfone matrix plates remains substantially the same, both before and after aging for one week at 122° F. and 90% relative humidity, while substantial increases are noted both before aging and after aging with the crosslinked CAB system. The increase is probably due to chemical and physical changes occurring in the plates.

While the present invention has been described in connection with certain preferred formulations and materials, it is not to be limited thereby but is to be limited solely by the scope of the claims which follow.

What is claimed is:

1. A humidity sensor element comprising:
   a thin, flexible film consisting essentially of a dielectric, water-absorbing first polymer having a dielectric constant which varies substantially linearly as a function of relative humidity,
   a pair of thin, water-permeable conductive layers disposed on opposite sides of said film and integrally bonded thereto, said conductive layers each consisting of a second polymer containing sulfur and having electrically conductive particles distributed therein, which conductive particles are effective to render said layers electrically conductive.

2. The element of claim 1 wherein said first polymer is a polyimide.

3. The element of claim 2 wherein the polyimide is sym-biphenyl tetracarboxylic acid dianhydride-p,p'-oxydianiline polyimide.

4. The element of claim 1 wherein the sulfur containing polymer is a polysulfone.

5. The element of claim 1 wherein the second polymer is a polyethersulfone.

6. The element of claim 1 wherein said conductive particles consist essentially of carbon particles.

7. The element of claim 6 wherein said carbon particles are chain forming to form agglomerates.

8. The element of claim 7 wherein the carbon particle agglomerates have an agglomerate size of about 10 microns or less.

9. The element of claim 6 wherein said conductive layers consist essentially of 10-80 wt./% of said carbon particles substantially uniformly distributed and 20-90 wt./% of the second polymer.

10. The element of claim 1 wherein the film has a thickness of 0.01 inch or less.

11. The element of claim 1 wherein the conductive layers each have a thickness of 0.005 inch or less.

12. The element of claim 1 wherein the conductive layers have a resistivity of 50,000 ohms/□ or less and the film has a resistivity of at least $10^{13}$ ohm-cm at 35° C. and 50% relative humidity.

13. The element of claim 12 wherein the conductive layers have a resistivity of 15,000 ohms/□ or less and the film has a resistivity of at least about $10^{15}$ ohm-cm at 35° C. and 50% relative humidity.

14. The element of claim 1 wherein the conductive particles consist essentially of chain-forming carbon particles having an agglomerate size of about 0.250 micron or less.

15. A method for making a humidity sensor element, comprising:
   (a) the step of disposing a piece of a thin, flexible film made of a dielectric, water absorbing first polymer having a dielectric constant which varies as a function of relative humidity on a holder;
   (b) the step of applying a stencil over the film;
   (c) screen printing the film through the stencil with a liquid composition comprising an electrically nonconductive second polymer containing sulfur, electrically conductive particles and a solvent;
   (d) the step of drying the liquid composition under conditions effective to form a water-permeable, first conductive layer on one side of the film and integrally bonded thereto, which conductive layer has a shape corresponding to the stencil; and
   (e) repeating steps b-d to form a second conductive layer on the face of the film opposite the first conductive layer.

16. The method of claim 15 wherein said first polymer is a polyimide.

17. The method of claim 16 wherein the polyimide is sym-biphenyl tetracarboxylic acid dianhydride-p,p'-oxydianiline polyimide.

18. The method of claim 15 wherein said second polymer is a polysulfone.

19. The method of claim 15 wherein the film has a thickness of 0.01 inch or less.

20. The method of claim 15 wherein the conductive layers each have a thickness of 0.005 inch or less.

* * * * *